(12) United States Patent
Sawada et al.

(10) Patent No.: US 9,709,752 B2
(45) Date of Patent: Jul. 18, 2017

(54) OPTICAL CONNECTOR PLUG, OPTICAL PROBE, AND OPTICAL SYSTEM

(75) Inventors: Atsushi Sawada, Chiyoda-ku (JP);
Kikuo Iwasaka, Chiyoda-ku (JP);
Yasuyuki Natsuno, Chiyoda-ku (JP)

(73) Assignee: Konica Minolta, Inc., Tokyo (JP)

( * ) Notice: Subject to any disclaimer, the term of this patent is extended or adjusted under 35 U.S.C. 154(b) by 828 days.

(21) Appl. No.: 14/118,505

(22) PCT Filed: May 17, 2012

(86) PCT No.: PCT/JP2012/003223
§ 371 (c)(1),
(2), (4) Date: Nov. 18, 2013

(87) PCT Pub. No.: WO2012/157276
PCT Pub. Date: Nov. 22, 2012

(65) Prior Publication Data
US 2014/0114198 A1    Apr. 24, 2014

(30) Foreign Application Priority Data

May 19, 2011  (JP) .................................. 2011-112606
May 19, 2011  (JP) .................................. 2011-112608

(51) Int. Cl.
*G02B 6/36*      (2006.01)
*G02B 6/38*      (2006.01)
*A61B 5/00*      (2006.01)

(52) U.S. Cl.
CPC .......... *G02B 6/3831* (2013.01); *A61B 5/0071* (2013.01); *G02B 6/387* (2013.01);
(Continued)

(58) Field of Classification Search
CPC .... G02B 6/3831; G02B 6/3826; G02B 6/387; G02B 6/3878
(Continued)

(56) References Cited

U.S. PATENT DOCUMENTS 4,687,291 A * 8/1987 Stape .................. G02B 6/3807
385/59
4,840,451 A     6/1989 Sampson et al.
(Continued)

FOREIGN PATENT DOCUMENTS

CN  1737628     2/2006
EP  0 339 876   4/1989
(Continued)

*Primary Examiner* — Jerry Blevins
(74) *Attorney, Agent, or Firm* — Cozen O'Connor

(57) ABSTRACT

Provided is an optical connector plug of which housing is provided with: a first member that has at least a lower surface section that covers the lower side of a providing space in which an optical fiber and a ferrule are provided, a half of a back surface section from which the optical fiber is led out, and a half of a front surface section from which the ferrule is led out, and is composite-molded out of a thermoplastic resin; and a second member that has at least an upper surface section that covers the upper side of the providing space, the remaining half of the back surface section and the remaining half of the front surface section, and is composite-molded out of a thermoplastic resin into the same shape as the first member.

6 Claims, 12 Drawing Sheets

(52) U.S. Cl.
CPC ......... *G02B 6/3826* (2013.01); *G02B 6/3878* (2013.01); *G02B 6/3821* (2013.01)

(58) Field of Classification Search
USPC ...................................................... 385/60, 78
See application file for complete search history.

(56) References Cited

U.S. PATENT DOCUMENTS

| | | |
|---|---|---|
| 4,944,568 A | 7/1990 | Danbach et al. |
| 5,231,685 A | 7/1993 | Hanzawa et al. |
| 5,501,606 A * | 3/1996 | Oda .................. H01R 13/631 439/140 |
| 6,244,753 B1 * | 6/2001 | O'Connor ................ G01J 3/44 385/12 |
| 2002/0181889 A1 | 12/2002 | Ozeki et al. |
| 2004/0008950 A1 | 1/2004 | Ozeki et al. |
| 2005/0185913 A1 | 8/2005 | Inamoto |
| 2006/0002662 A1 | 1/2006 | Manning et al. |
| 2010/0329605 A1 * | 12/2010 | Graham ............... G02B 6/4207 385/33 |

FOREIGN PATENT DOCUMENTS

| | | |
|---|---|---|
| JP | 60-84910 | 6/1985 |
| JP | 084910/1985 | 6/1985 |
| JP | 60-110808 | 7/1985 |
| JP | 203891/1983 | 7/1985 |
| JP | 61-502356 | 10/1986 |
| JP | 01-188809 | 7/1989 |
| JP | 01-316711 | 12/1989 |
| JP | 03-100504 | 4/1991 |
| JP | 06-059156 | 3/1994 |
| JP | 09-304652 | 11/1997 |
| JP | 10-160966 | 6/1998 |
| JP | 2001-133658 | 5/2001 |
| JP | 2001-515597 | 9/2001 |
| JP | 2005-234498 | 9/2005 |
| JP | 2005-241758 | 9/2005 |
| JP | 2006-018296 | 1/2006 |
| JP | 2006-330088 | 12/2006 |
| JP | 2008-046433 | 2/2008 |
| JP | 2011-002709 | 1/2011 |
| WO | WO 86/00147 | 1/1986 |

* cited by examiner

OPTICAL CONNECTOR PLUG, OPTICAL PROBE, AND OPTICAL SYSTEM

RELATED APPLICATIONS

This application is a U.S. National Phase Application under 35 USC 371 of International Application PCT/JP2012/003223 filed May 17, 2012.

This application claims the priority of Japanese application Nos. 2011-112606 filed May 19, 2011 and 2011-112608 filed May 19, 2011, the entire content of both of which are hereby incorporated by reference.

TECHNICAL FIELD

The present invention relates to an optical connector plug, and an optical probe and an optical system using this optical connector plug.

BACKGROUND ART

In recent years, a diagnostic method is known which includes inserting an endoscope into a human body with an optical probe introduced through the endoscope, irradiating thereafter a site to be diagnosed inside the body with excitation light via this optical probe, measuring fluorescence generated by the excitation light and inspecting and/or analyzing the site to be diagnosed. Since the optical probe is inserted into the human body in this diagnostic method, it is desirable to replace the optical probe with a new one every time it is used. Therefore, there is a demand for a further cost reduction of the optical probe.

The optical probe is constructed of an optical connector plug to be connected to an optical apparatus, an optical cable composed of a plurality of optical fibers inserted into a tube to emit excitation light and illumination light and capture fluorescence from a distal end, and the like.

Furthermore, as a prior art related to the present invention, PTL 1 discloses an optical connector plug capable of connecting a plurality of optical routes at a time.

CITATION LIST

Patent Literature

PTL 1
U.S. Pat. No. 5,231,685

SUMMARY OF INVENTION

Technical Problem

A large number of parts as in the case of the above conventional optical connector plug complicates the assembly steps, which leads to an increase in the manufacturing cost. Moreover, when there is a plurality of types of non-generic resin molded products, it is necessary to manufacture one metal die per type, which leads to a drastic cost increase.

Conventional optical connector plugs for optical communication are designed on the assumption that each component is molded with high accuracy to reduce transmission loss of light. Therefore, it is difficult to achieve a cost reduction for the optical connector plug as it is.

On the other hand, when the molding accuracy of components such as a housing is lowered to reduce the manufacturing cost of the optical connector plug, it is difficult to accurately connect the plug and a receptacle due to dimensional errors in the components. In the case of an optical connector plug which connects a plurality of optical routes at a time in particular, minuscule errors in distances among the plurality of optical routes between the plug side and the receptacle side may make it difficult to smoothly connect the plug and the receptacle.

An object of the present invention is to provide an optical connector plug that allows the number of parts or the number of types thereof to be reduced for a cost reduction, and an optical probe and an optical system using this optical connector plug.

Another object of the present invention is to provide an optical connector plug with a smaller number of parts and allowing an accurate connection to an optical connector receptacle even when molding accuracy of a housing is lowered, and an optical probe and an optical system using this optical connector plug.

Solution to Problem

An optical connector plug according to one aspect of the present invention is an optical connector plug including an optical fiber and a ferrule to which the optical fiber is connected, and a housing that covers the optical fiber and the ferrule, wherein the housing includes a first member including at least an undersurface portion that covers an underside of an arrangement space in which the optical fiber and the ferrule are arranged, a half of a rear surface portion from which the optical fiber is led out and a half of a front surface portion from which the ferrule is led out, the undersurface portion, the half of the rear surface portion and the half of the front surface portion being integrally molded of thermoplastic resin; and a second member including at least a top surface portion that covers an upper side of the arrangement space, the remaining half of the rear surface portion and the remaining half of the front surface portion, the top surface portion, the remaining half of the rear surface portion and the remaining half of the front surface portion being integrally molded of thermoplastic resin into a shape identical to the shape of the first member.

Another aspect of an optical connector plug according to the present invention includes a housing, a ferrule to which an optical fiber is connected, and a holding member including a fixing section fixed to the housing, a holding section that holds the ferrule and a spring section that is bent between the fixing section and the holding section by an external force, the fixing section, the holding section and the spring section being integrally molded of thermoplastic resin, wherein the ferrule is fixed to the housing via the holding member in a manner displaceable by bending of the spring section.

Advantageous Effects of Invention

According to the present invention, the housing can be mainly constructed of the first member and the second member, and the number of parts can thereby be reduced. Since the first member and the second member have an identical shape, both members can be molded using the same metal die. As a result, it is possible to achieve a further cost reduction of the optical connector plug.

According to the present invention, the number of parts of the optical connector plug is reduced, which can contribute to a cost reduction of the optical connector plug. Even when the housing contains a molding error, bending of the spring section of the holding member can absorb this molding error, allowing the optical axis of the ferrule to accurately coincide with the optical axis of a receptacle which is the connection mate. Therefore, it is possible to slightly reduce the molding error of the housing and thereby achieve a cost reduction of the optical connector plug.

DESCRIPTION OF EMBODIMENTS

Hereinafter, an embodiment of the present invention will be described with reference to the accompanying drawings.

Figure 1A:
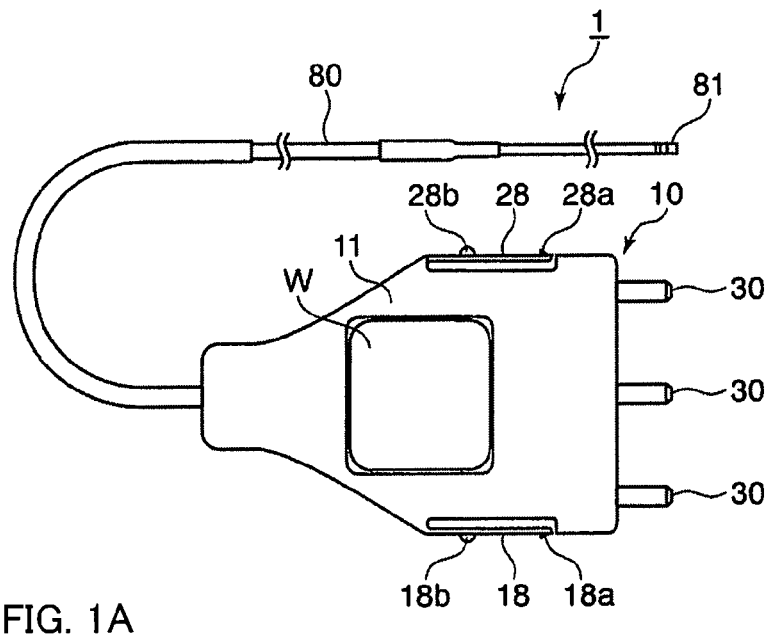
FIGS. 1A to 1C are trihedral figures illustrating an optical probe according to an embodiment of the present invention and FIG. 1D is a bottom view thereof.
Figure 1B:
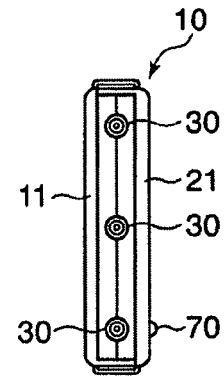
Figure 1C:
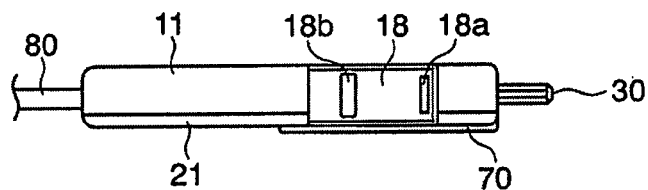
Figure 1D:
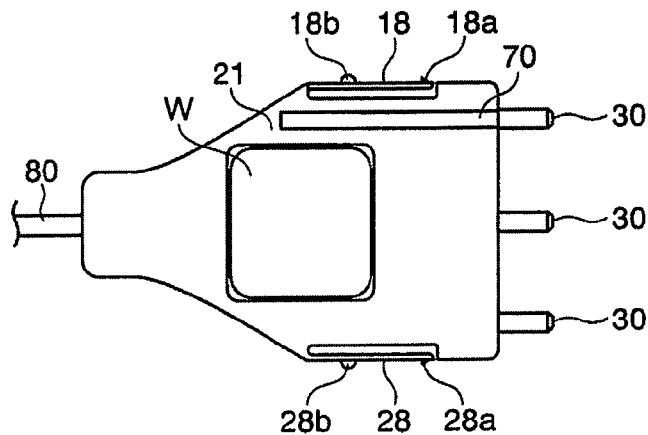

FIGS. 1A to 1D illustrate an optical probe of the present embodiment. FIG. 1A is a top view thereof; FIG. 1B is a front view, FIG. 1C is a side view and FIG. 1D is a bottom view.

Optical probe 1 of the present embodiment is a probe intended to perform an inspection and/or analysis of a site to be diagnosed in a human body through fluorescence detection and is constructed of optical connector plug 10 connected to optical apparatus 100 (see FIG. 11) and cable 80, a distal end side of which is passed through an endoscope and inserted into a human body. Cable 80 is constructed such that plural optical fibers 85 (see FIG. 11) are inserted therein, and respective distal ends of the plurality of optical fibers 85 and a condensing lens are fixed to distal end 81.

Optical connector plug 10 is constructed of first member 21 and second member 11 that constitute a housing, three ferrules 30 and three holding members 50 (see FIG. 8) for respectively fixing ferrules 30 to the housing or the like.

Figure 2A:
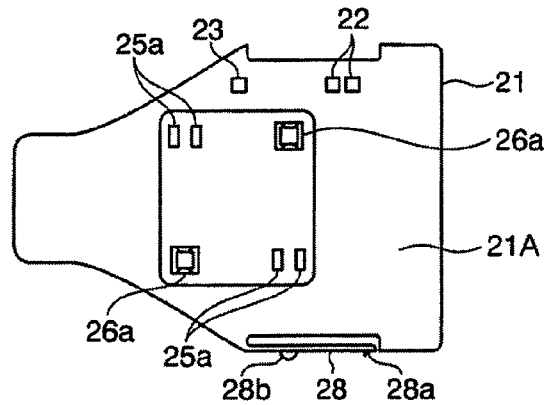
FIGS. 2A to 2F are hexahedral figures illustrating a first member of a housing of an optical connector plug and FIG. 2G is a cross-sectional view along line A-A in FIG. 1C.
Figure 2B:
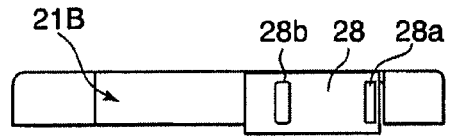
Figures 2C, 2D, 2E:
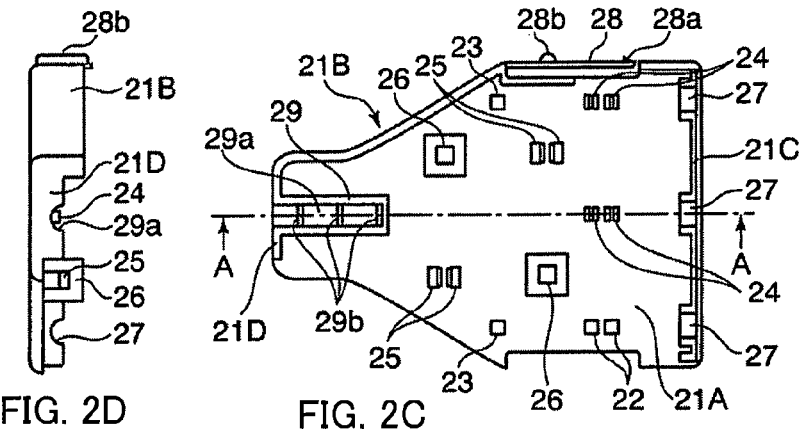

FIGS. 2A to 2G illustrate a bottom view, a right side view, a plan view, a rear view, a front view, a left side view and a cross-sectional view along line A-A of first member 21 respectively. FIGS. 3A and 3B illustrate a rear view and a plan view of second member 11 respectively.

As shown in FIGS. 2A to 2G, first member 21 is composed of undersurface portion 21A that covers an underside of an arrangement space in which ferrules 30 and optical fibers 85 are arranged, right side portion 21B, front surface portion 21C that occupies a half of a front surface from which ferrules 30 are led out and rear surface portion 21D that occupies a half of a rear surface from which optical fibers 85 are led out, all of which are integrally molded through injection molding of thermoplastic resin.

Three semicircular grooves 27 for leading three ferrules 30 outward are arranged side by side on front surface portion 21C. Semicircular grooves 27 are formed at a height position half that of the housing and constitute, together with similar semicircular grooves 17 (see FIGS. 3A and 3B) of second member 11, circular through holes.

Rear surface portion 21D is provided with semicanal groove (cable holding groove) 29a of a predetermined length for leading cable 80 containing plural optical fibers 85 outward. Semicanal groove 29a is provided in swelling portion 29 that swells from undersurface portion 21A so as to be arranged at a height position half that of the housing, mated with a similar semicanal groove 19a (see FIGS. 3A and 3B) of second member 11 to constitute a tubular path which is open inside and outside the housing to hold cable 80. Semicanal groove 29a is provided with a plurality of lateral grooves 29b orthogonal to the longitudinal direction and flange 83a of binding hardware 83, which will be described later, can be fitted into lateral groove 29b.

Undersurface portion 21A is formed into a polygonal shape (a polygon whose angles are rounded) which is narrow on the rear side and wide on the front side of optical connector plug 10. Undersurface portion 21A is provided with engaging sections (snap-fit or the like) 24 respectively at positions opposed to two of three semicircular grooves 27, that is, right and center semicircular grooves 27 to bind holding members 50 by a one-touch operation. Engaging section 24 has a general configuration, composed of, for example, two piece members arranged side by side standing upright and spaced apart so that the distal end side can be opened or closed through bending and provided with stopper lugs (locking lugs) outside the respective piece members. The two piece members are passed through an insertion hole of a small width that allows the two piece members to be inserted until they come out, so that engaging section 24 is fitted into the insertion hole with a certain strength or higher.

Mounting holes (insertion holes) 22, 22 and 23 for mounting up/down orientation identification protrusion 70 (see FIGS. 1A to 1D) as an orientation identification member are provided at positions opposed to one semicircular groove 27 on the left instead of engaging sections 24. Locking pieces of protrusion 70 are passed through mounting holes 22 and 22 from outside so as to protrude inside undersurface portion 21A. Therefore, the protruding portions are formed into a shape substantially identical to that of engaging section 24 so that when protrusion 70 is attached, a configuration similar to engaging section 24 also appears in mounting holes 22 and 22, making it possible to bind holding member 50 with this portion.

Undersurface portion 21A is provided with a plurality of engaging sections 25 and engaged sections 26 for coupling with second member 11. Engaging section 25 has a configuration similar to that of aforementioned engaging section (snap-fit) 24 with only differences in height and width. Engaged section 26 is configured of an insertion hole formed on the top of a block swelling from undersurface portion 21A to provide a height. These engaging section 25 and engaged section 26 are formed at positions half the height of the housing or higher so as to be able to engage with similar engaged section 16 and engaging section 15 of second member 11 respectively. That is, engaging section 25 and engaged section 26 are formed to such heights that allow insertion holes of engaged sections 16 and 26 to reach lugs of engaging sections 15 and 25. As shown in FIG. 2A and FIG. 3A, grooves 25a and 26a (grooves 15a and 16a in second member 11) are formed on back sides of engaging section 25 and engaged section 26 to fill in with resin through injection molding and to disengage the engagement between engaging section 25 and engaged section 26 by inserting a screw driver or the like thereinto, and these grooves 25a and 26a are sealed with a seal W (see FIG. 1D).

These engaging sections 25 and engaged sections 26 are provided at symmetric positions of the housing. Such an arrangement allows engaging sections 15 and engaged sections 16 of second member 11 to be in a similar arrangement (see FIG. 3B) and to engage with their respective counterparts.

Figure 2G:
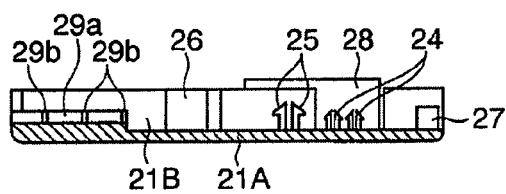
Figure 2F:
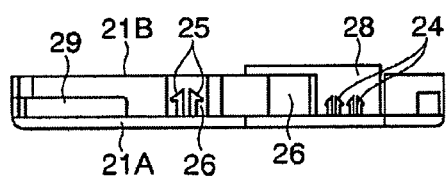
Figure 3A:
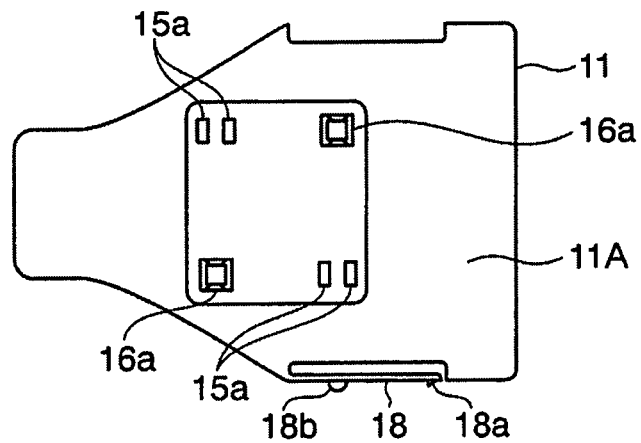
FIGS. 3A and 3B are a plan view and a rear view respectively illustrating a second member of the housing.
Figure 3B:
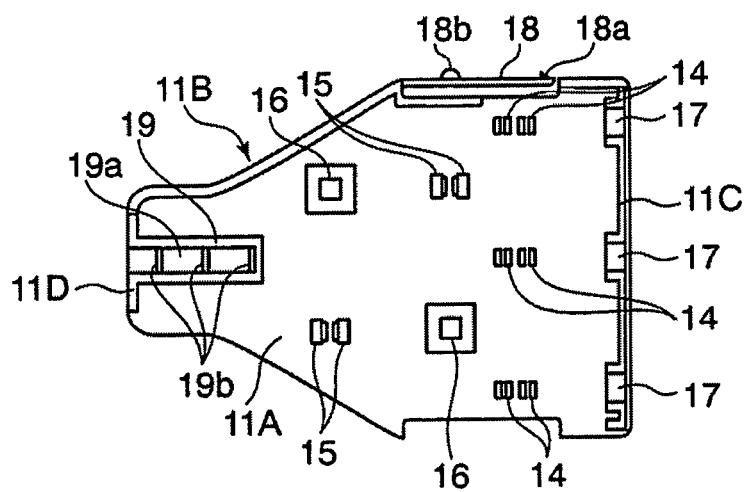

As shown in FIG. 2F and FIG. 2G, engaging sections 25 are two piece members arranged side by side in an anteroposterior direction (direction from rear surface portion 21D to front surface portion 21C). The two piece members of engaging section 25 are slightly displaced by bending in the direction in which they are arranged, whereas they are hardly displaced in a crosswise direction orthogonal to the direction in which they are arranged because they are thick in that direction. For this reason, when engaging section 25 is engaged with engaged section 16 of the first member, engaging section 25 and engaged section 16 are fixed in the crosswise direction more firmly than in the anteroposterior direction. First member 21 and second member 11 constituting the housing have a configuration in which one of the right and left sides is not formed at all and the right and left sides of the housing are designed to be pinched and held by a user. For this reason, it is convenient if first member 21 and second member 11 can be fixed firmly in the crosswise direction. Thus, because of the aforementioned arrangement of the two piece members of engaging section 25, the engagement between engaging section 25 and engaged section 16 strengthens the fixing in the crosswise direction.

Figure 11:
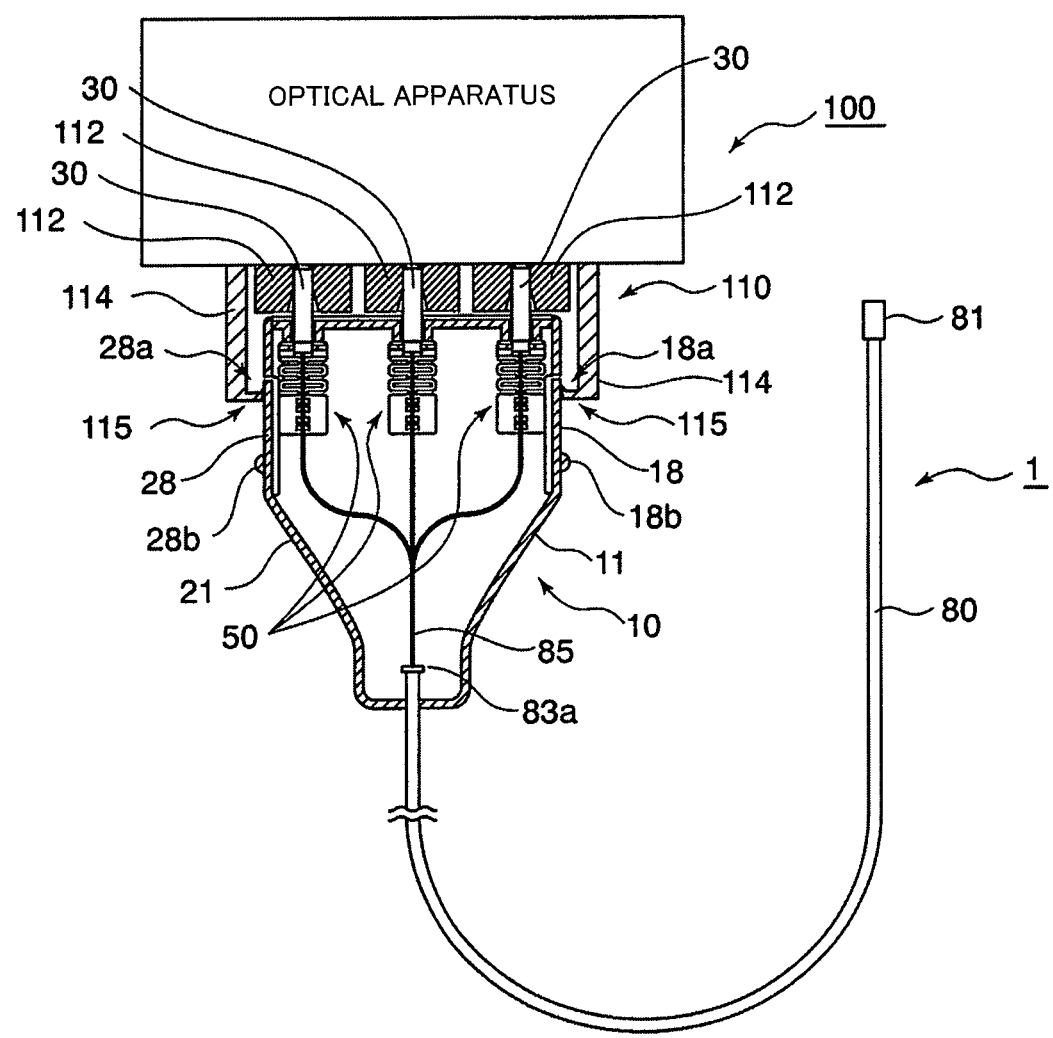
FIG. 11 is a partially cutaway plan view illustrating the optical probe connected to an optical apparatus.

Right side portion 21B makes up a side wall that covers the right side of the housing and is provided with a flat-spring-shaped locking piece (plug locking portion) 28 in its entirety that locks optical connector plug 10 to optical connector receptacle 110 when connecting optical connector plug 10 to optical connector receptacle 110 of optical apparatus 100 (see FIG. 11). Locking piece 28 has a cantilever structure in which a proximal end thereof is supported and a distal end side is left free, and provided with locking lug 28a outside at the end and convex portion 28b for preventing slippage outside in a midway position. A gap for making the distal end of locking piece 28 movable inward is provided between locking piece 28 and undersurface portion 21A, and between locking piece 28 and part of the side wall of right side portion 21B.

As shown in FIGS. 3A and 3B, second member 11 is composed of top surface portion 11A that covers a top surface of an arrangement space in which ferrules 30 and optical fibers 85 are arranged, left side portion 11B, front surface portion 11C that occupies a half of the front surface from which ferrules 30 are led out and rear surface portion 11D that occupies a half of the rear surface from which optical fibers 85 are led out, all of which are integrally formed through injection molding of thermoplastic resin.

Second member 11 has a shape substantially identical to that of first member 21 and is arranged in a substantially identical configuration and at a substantially identical position. That is, as in the case of engaging sections 24 and 25, engaged section 26, three semicircular grooves 27, locking piece 28 and semicanal groove 29a of first member 21, second member 11 is provided with engaging sections 14 and 15, engaged section 16, three semicircular grooves 17, locking piece 18 and semicanal groove 19a at the same positions and in the same directions. As in the case of locking piece 28 of first member 21, locking piece 18 is provided with locking lug 18a and convex portion 18b, semicanal groove 19a is formed in swelling portion 19 in the same way as semicanal groove 29a of first member 21 and has a plurality of lateral grooves 19b.

However, second member 11 is not provided with a configuration similar to the configuration of mounting holes 22 and 23 to mount protrusion 70 for up/down orientation identification, but provided instead with engaging section 14 for fixing holding member 50 at a position opposed to semicircular groove 27 on the left as well. Replacement between small mounting holes 22 and 23, and small engaging section 14 formed on a flat plate can be realized by replacing some accessory metal dies for an identical basic metal die. Therefore, first member 21 and second member 11 can be molded using a common basic metal die or are molded using a common basic metal die.

Figure 4A:
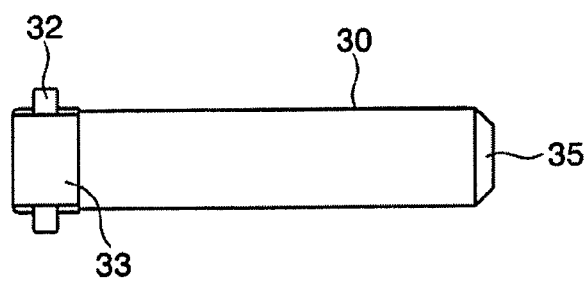
FIGS. 4A to 4C are trihedral figures illustrating a ferrule.
Figure 4C:
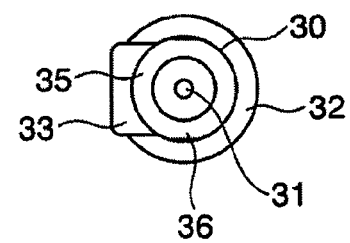
Figure 4B:
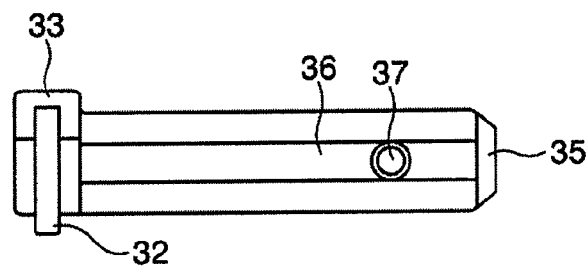
Figure 6:
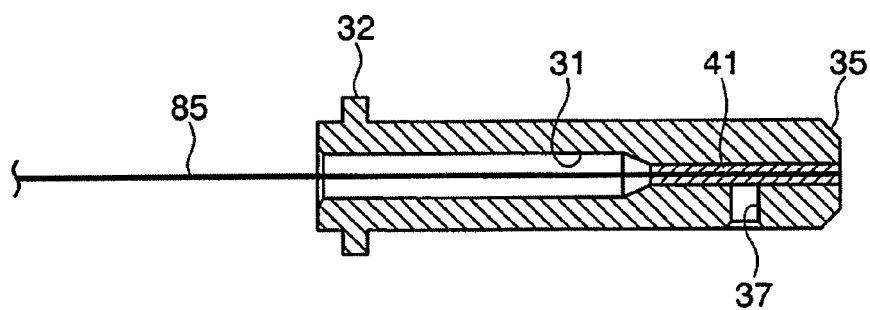
FIG. 6 is a cross-sectional view illustrating the ferrule in which an optical fiber is inserted.

FIGS. 4A to 4C illustrate a plan view, a side view and a front view of ferrule 30 respectively and FIG. 6 is a cross-sectional view of ferrule 30 in which optical fiber 85 is inserted.

As shown in FIGS. 4A to 4C and FIG. 6, ferrule 30 is a columnar member through which optical fiber 85 is inserted and which allows the fiber end surface to be arranged in the center of the distal end, and is, for example, injection-molded of thermoplastic resin. Ferrule 30 is provided with through hole 31 at the center which is formed from the proximal end to the distal end thereof, tapered portion 35 of a small diameter at the distal end formed outside at the distal end, flat surface portion 36 which is a partial range in the circumferential direction of the columnar portion chamfered into a flat shape along the axial direction, lateral hole 37 formed from flat surface portion 36 to through hole 31, circular flange 32 formed at the root of the ferrule, and rectangular flange 33 that extends in the diameter direction so as to overlap with circular flange 32 only within a partial angle range in the circumferential direction and is formed to be thicker than circular flange 32 in the axial direction.

As shown in FIG. 6, through hole 31 in the center of ferrule 30 is formed so as to have a large diameter on the root side and a small diameter substantially equal to that of inner ferrule 41 on the distal end side. Optical fiber 85 is fixed to ferrule 30 as follows. That is, a cable conductor of optical fiber 85 is passed through inner ferrule 41 and fixed using an adhesive or the like first, and the distal end thereof is polished together with inner ferrule 41. Then, inner ferrule 41 connected with optical fiber 85 is inserted through through hole 31 of ferrule 30, and end surfaces of inner ferrule 41 and ferrule 30 are adjusted to be flush with each other. In this condition, an adhesive or a screw is inserted as a fixing member via lateral hole 37 and inner ferrule 41 is fixed to through hole 31. Inner ferrule 41 is made of metal, although it is not particularly limited.

Figure 5A:
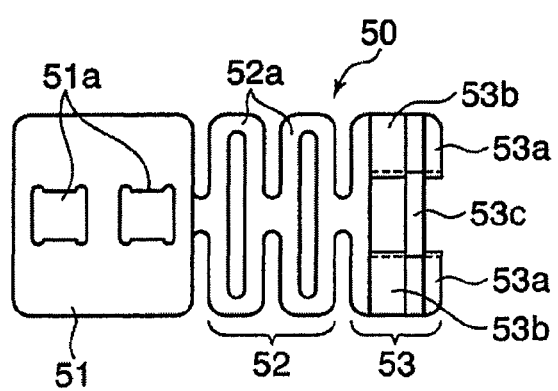
FIGS. 5A to 5C are trihedral figures illustrating a holding member.
Figure 5C:
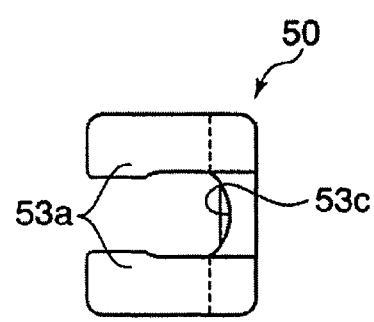
Figure 5B:
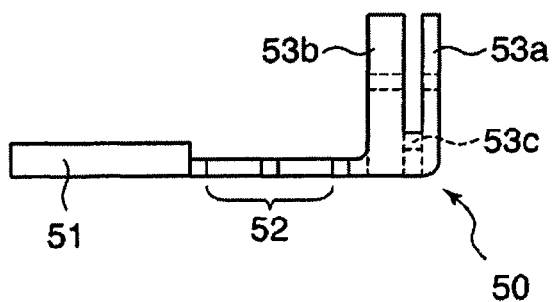
Figure 7C:
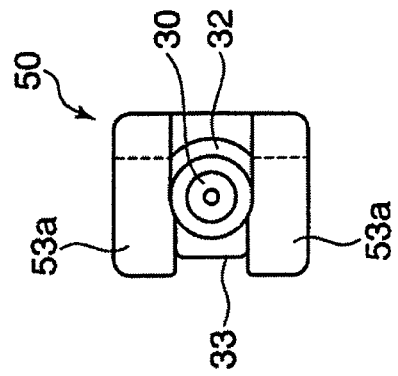
FIGS. 7A to 7C are trihedral figures illustrating the ferrule held by the holding member.
Figure 7A:
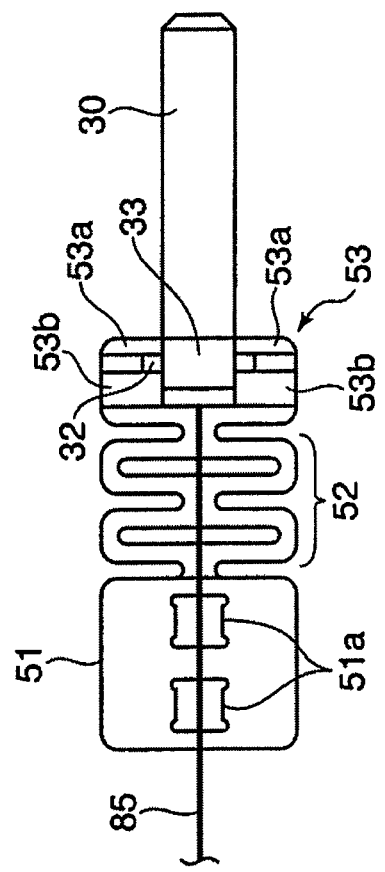
Figure 7B:
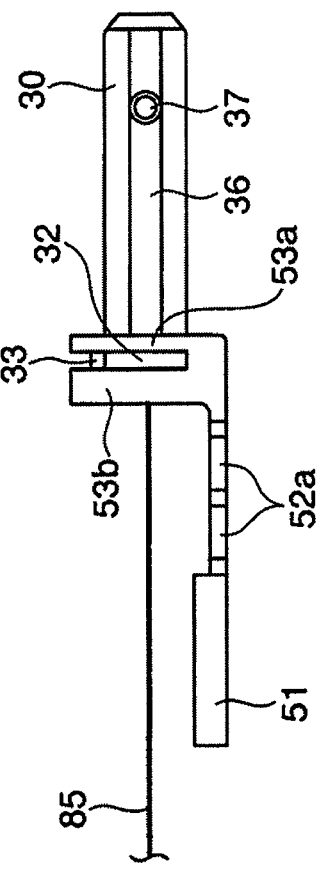

FIGS. 5A to 5C illustrate a plan view, a side view and a front view of holding member 50, and FIGS. 7A to 7C illustrates trihedral figures of ferrule 30 held by holding member 50.

As shown in FIGS. 5A to 5C and FIGS. 7A to 7C, holding member 50 is provided with fixing section 51 fixed to the housing (first member 21 or second member 11), holding section 53 that holds the root portion of ferrule 30, and spring section 52 that bends to cause holding section 53 to displace in vertical/crosswise/anteroposterior directions by an external force. Fixing section 51 is configured of two insertion holes 51a and 51a formed on a flat plate, engaging sections 14 and 14 (or engaging sections 24 and 24) are inserted through insertion holes 51a and 51a and both are then coupled together. Spring section 52 is configured by connecting into line, a plurality of rings 52a and 52a formed to have a thickness so as to bend with appropriate hardness and a small width in one direction.

Holding section 53 is configured of four pinching pieces 53a, 53a, and 53b, 53b standing upright from the bottom surface portion on a block. Gaps for bringing into close contact and pinching circular flange 32 of ferrule 30 are provided before and after four pinching pieces 53a, 53a, and 53b, 53b, and gaps for bringing into close contact and pinching rectangular flange 33 and the columnar portion of ferrule 30 are provided between the right and left sides of four pinching pieces 53a, 53a, and 53b, 53b. These gaps constitute fitting grooves. A curved surface having the same curvature as that of the circumferential surface of circular flange 32 is formed on center bottom surface portion 53c of the gaps sandwiching circular flange 32. Moreover, gaps between the right and left sides are formed so as to become slightly narrower partially along the circumferential surface of the columnar portion of ferrule 30 from the middle to the distal end side of four pinching pieces 53a, 53a, and 53b, 53b.

In such a configuration, rectangular flange 33 of ferrule 30 is placed face up, the portion of circular flange 32 of ferrule 30 is inserted from above into an arrangement space between four pinching pieces 53a, 53a, and 53b, 53b, and ferrule 30 can thereby be uniformly held to holding section 53. At this time, as shown in FIG. 7A, rectangular flange 33 is pinched by four pinching pieces 53a, 53a, and 53b, 53b, which prevents rectangular flange 33 from rotating about the axis of ferrule 30 with respect to holding section 53. Moreover, as shown in FIG. 7C, the underside of the circumferential surface of circular flange 32 comes into close contact with center bottom surface portion 53a and the columnar portion of ferrule 30 is inserted into the crosswise gap between four pinching piece 53a, 53a, and 53b, 53b, which prevents ferrule 30 from moving in the vertical direction (crosswise direction in FIG. 7C) with respect to holding section 53.

Figure 8:
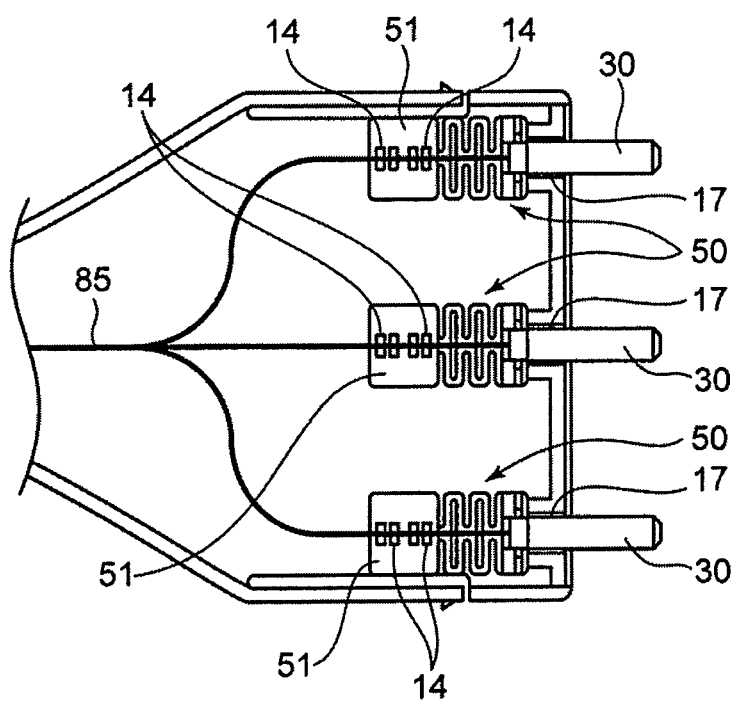
FIG. 8 is a plan view illustrating the holding member and the optical fiber fixed to the housing.
Figure 9:
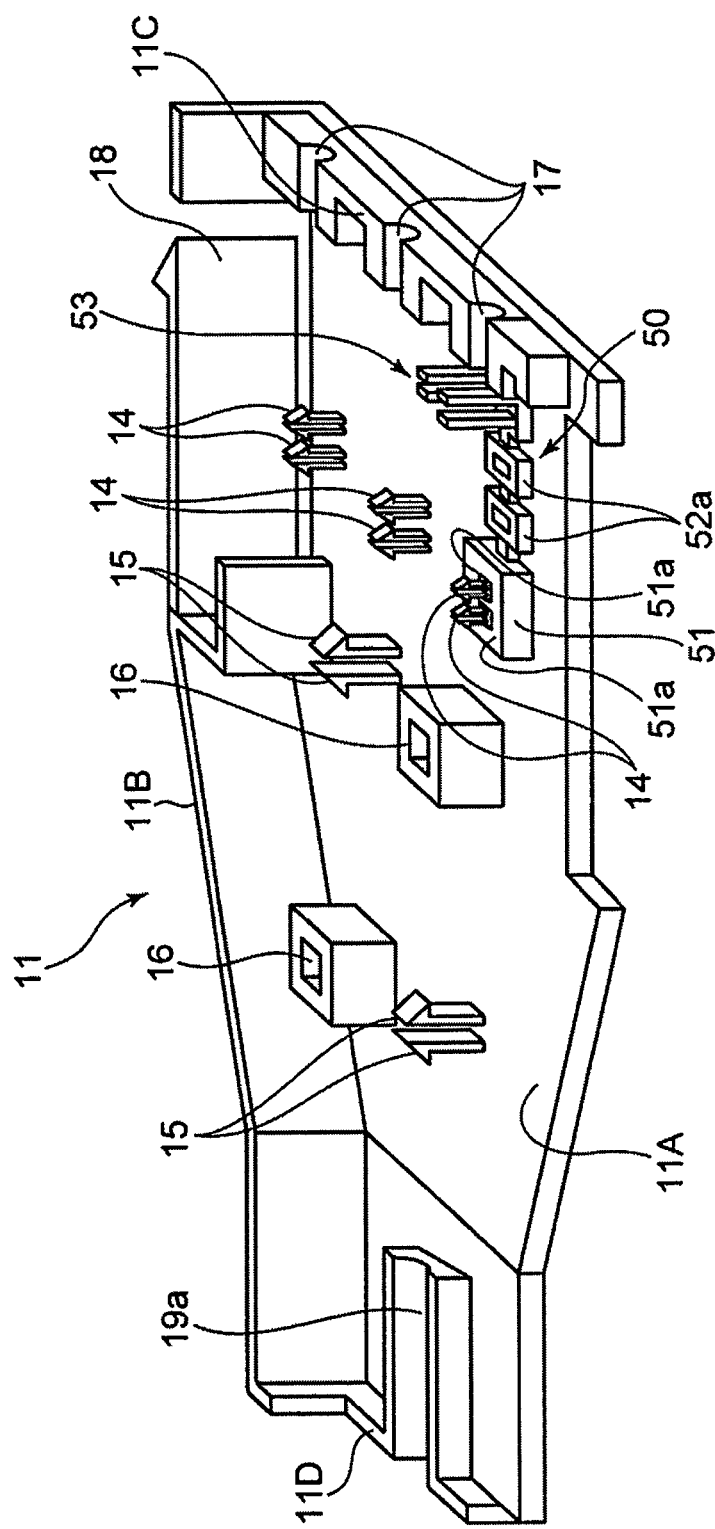
FIG. 9 is a perspective view illustrating one holding member fixed to the housing.

FIG. 8 illustrates a plan view of holding member 50 and optical fiber 85 fixed to the housing and FIG. 9 illustrates a perspective view of one holding member 50 fixed to the housing. As shown in FIG. 8 and FIG. 9, engaging sections 14 and 14 of second member 11 are passed through insertion holes 51a and 51a respectively until lugs thereof come out, and fixing section 51 of holding member 50 is thereby fixed to second member 11. At this time, as shown in FIG. 8, ferrule 30 held by holding section 53 of holding member 50 is arranged along semicircular groove 17 of second member 11.

Moreover, when first member 21 and second member 11 of the housing are mated together, as shown in FIG. 1B, semicircular groove 27 of first member 21 and semicircular groove 17 of second member 11 are coupled together to form a cylindrical hole (through hole) and ferrule 30 is led out from the cylindrical hole. A small gap is provided between the cylindrical hole and ferrule 30, and through the bending of spring section 52 of holding member 50, ferrule 30 can be displaced in anteroposterior (direction along the optical axis), vertical and crosswise (direction perpendicular to the optical axis) directions within a range of a predetermined length, and the distal end of ferrule 30 can be displaced in a rotating direction around the vicinity of the root of ferrule 30 within a range of a predetermined length. A range of a predetermined length of optical fiber 85 from the proximal end of ferrule 30 is arranged in a manner slightly displaceable in the housing to prevent the movement of ferrule 30 from being blocked as described above.

Figure 10:
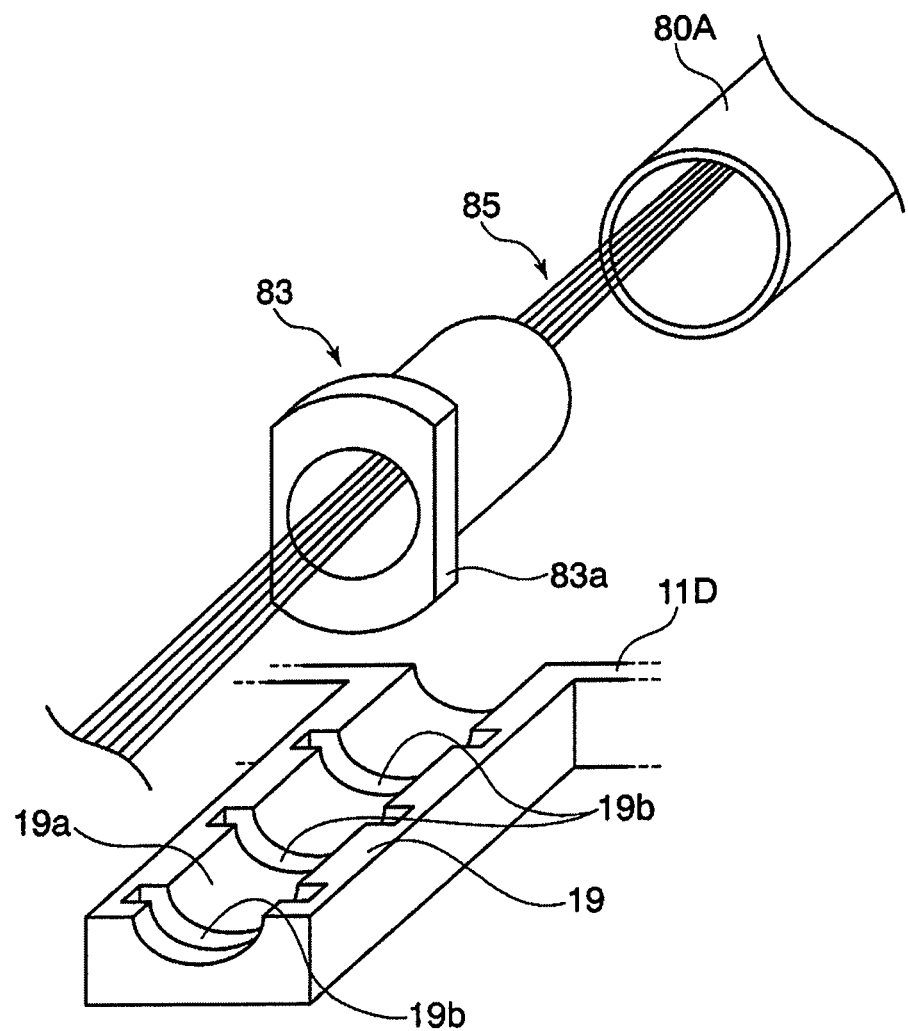
FIG. 10 is a perspective view illustrating a structure of fixing the optical fiber and a cable of the housing.

FIG. 10 is a perspective view illustrating a structure of fixing optical fiber 85 and cable 80 of the housing. As shown in this figure, plural optical fibers 85 connected to three ferrules 30 are fixed to the proximal end of the housing via binding hardware 83 and led out of the connector. One optical fiber 85 on which excitation light enters from optical apparatus 100 and one optical fiber 85 that sends detected fluorescence to optical apparatus 100 are each connected to right and left ferrules 30 and 30 of three ferrules 30. On the other hand, since plural optical fibers 85 for illumination are connected to one ferrule 30 in the center, the total number of optical fibers 85 is more than three.

Binding hardware 83 is configured of a cylindrical body through which plural optical fibers 85 are passed, provided with fixing flange 83a. Flange 83a has a rotationally asymmetric shape. Plural optical fibers 85 are passed through binding hardware 83 and fixed using an adhesive or the like and tube 80A of cable 80 is fitted with the cylindrical portion of binding hardware 83 and fixed. The cylindrical portion of binding hardware 83 is sandwiched between semicanal grooves 19a and 29a of first member 21 and second member 11 of the housing, flange 83a of binding hardware 83 is fitted with one of plural lateral grooves 19b and 29b and thereby fixed to the housing while preventing cable 80 from rotating. Binding hardware 83 may be formed of resin.

Figure 12:
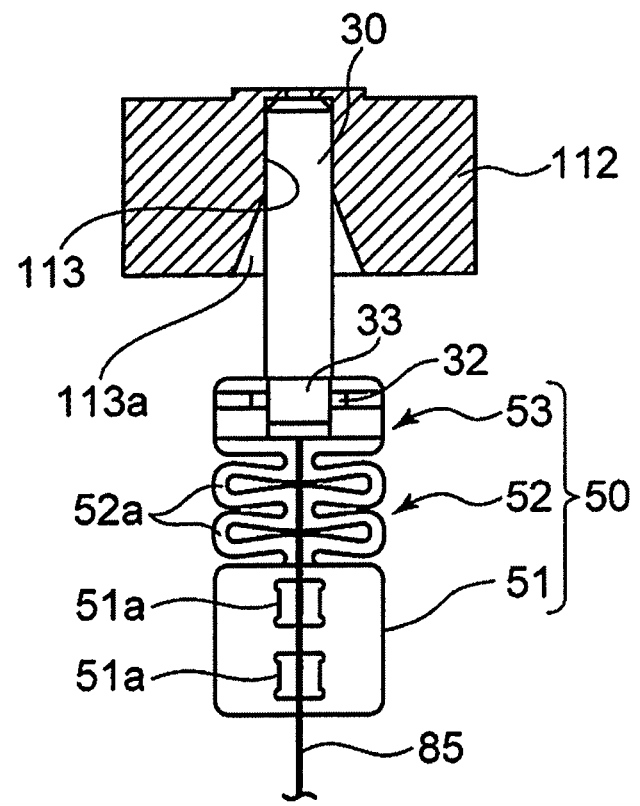
FIG. 12 is an enlarged view illustrating the periphery of the ferrule with the optical probe connected to the optical apparatus.

FIG. 11 is a partially cutaway plan view of optical probe 1 connected to optical apparatus 100 and FIG. 12 is an enlarged view of the periphery of ferrule 30 when the connector is connected.

An optical system of the present embodiment is constructed of optical apparatus 100 to which three optical routes of optical probe 1 are connected to emit excitation light and illumination light and input fluorescence, and optical probe 1 having above-described optical connector plug 10. Optical apparatus 100 is provided with optical connector receptacle 110 to which optical connector plug 10 is connected to input/output light as described above.

Optical connector receptacle 110 is provided with three receptacle parts 112 connected in such a way that the optical axis is adjusted with respect to ferrules 30, and receptacle case 114 that covers the outside of three receptacle parts 112 and has an opening into which the distal end side of optical connector plug 10 is inserted.

Receptacle part 112 has sleeve hole (insertion port) 113 that allows ferrule 30 to be inserted with the distal end thereof fixed, and an optical route (optical fiber stub, lens or the like) is arranged at the center of the end surface of sleeve hole 113 with the optical axis thereof adjusted. Taper 113a whose diameter increases toward the entrance side within a range of at least ⅓ of length is provided on the entrance side of sleeve hole 113 so as to guide the distal end of ferrule 30 and guide the optical axis of ferrule 30 to the center of the end surface of sleeve hole 113.

In such a configuration, optical connector plug 10 is pushed into the opening of receptacle case 114, three ferrules 30 are thereby inserted into sleeve holes 113 of three receptacle parts 112 so that the distal ends of ferrules 30 are guided by taper 113a to the end where there is less clearance and positioned/fixed even when there is a little misalignment. At this time, as shown in FIG. 12, spring section 52 of holding member 50 of ferrule 30 is bent so as to absorb any small error in the housing of optical connector plug 10 and allows three ferrules 30 to be fixed with ferrules 30 being pushed against the end surfaces of three receptacle parts 112.

Locked portions 115 and 115 are provided on the right and left sides of the opening of receptacle case 114 so that when optical connector plug 10 is connected, locking lugs 18a and 28a of locking pieces 18 and 28 are hooked at locked portions 115 and 115 and locked. When optical connector plug 10 is disconnected, by pulling optical connector plug 10 while pushing convex portions 18b and 28b of locking pieces 18 and 28 inward, locking pieces 18 and 28 are unlocked from locked portions 115 and 115 of receptacle case 114 and both portions can thereby be detached.

In the optical system configured as described above, a medical doctor connects new optical probe 1 to optical apparatus 100, passes the probe distal end side of optical probe 1 through the tube of an endoscope and inserts the whole endoscope into a human body. The medical doctor then finds out a site to be diagnosed inside the body while watching video of the endoscope, causes the distal end of optical probe 1 to come out from the distal end of the endoscope and directs the distal end of optical probe 1 to the site to be diagnosed. The medical doctor then starts processing of fluorescence detection. When the processing for fluorescence detection starts, illumination of the endoscope is turned off and switched to illumination of optical probe 1. When operation of fluorescence detection by optical apparatus 100 is performed in this condition, illumination of optical probe 1 is instantaneously stopped and excitation light is outputted in the meantime to radiate the site to be diagnosed via one optical fiber 85 of optical probe 1, fluorescence emitted immediately thereafter by the excitation light is sent to optical apparatus 100 via other one optical fiber 85 of optical probe 1 and light quantity or the like is measured. An analysis of the site to be diagnosed is performed based on the light quantity of this fluorescence. When the processing of the fluorescence detection is completed, cable 80 of optical probe 1 is pulled out from the endoscope, optical connector plug 10 is also disconnected from optical apparatus 100 and this optical probe 1 is disposed of.

As described above, in optical connector plug 10, optical probe 1 and the optical system of the present embodiment, the housing of optical connector plug 10 is composed of two parts: first member 21 and second member 11 and the number of parts of optical connector plug 10 is thereby reduced. Moreover, since first member 21 and second member 11 have the same shape, both members can be molded using the same metal die. Therefore, the manufacturing cost of optical connector plug 10 can be drastically reduced.

One of locking pieces 18 and 28 arranged on opposite sides of optical connector plug 10 of the present embodiment is provided integrally with first member 21 and the other is provided integrally with second member 11. Therefore, the number of parts is not increased to add a configuration for locking optical connector plug 10 to optical connector receptacle 110. Moreover, since first member 21 and second member 11 are provided with one or the other of locking pieces 18 and 28 respectively, it is possible to prevent one locking piece 18 (28) from being divided into first member 21 and second member 11, resulting in a complicated structure.

Since first member 21 and second member 11 are provided with engaging sections 15 and 25, and engaged sections 16 and 26 respectively, any additional part for coupling first member 21 and second member 11 is not necessary. Since engaging sections 15 and 25, and engaged sections 16 and 26 are provided at symmetric positions, engaging sections 15 and 25, and engaged sections 16 and 26 can be placed in the same arrangement between first member 21 and second member 11 so that both can engage with each other. Therefore, first member 21 and second member 11 can be formed using the same metal die.

Furthermore, since a pair of piece members of engaging section 15 or 25 are provided so as to align in an anteroposterior direction, it is possible to firmly fix first member 21 and second member 11 in a crosswise direction. Therefore, as described above, when the housing is held from opposite sides, it is possible to prevent first member 21 and second member 11 from displacing from each other.

Since first member 21 is provided with protrusion 70 for up/down orientation identification on the outer surface thereof, even when the housing is formed into a shape symmetric in vertical and crosswise directions, it is possible to connect optical connector plug 10 to optical connector receptacle 110 while correctly recognizing the vertical and crosswise directions of optical connector plug 10. Regarding protrusion 70, since first member 21 and second member 11 are different only in the presence or absence of mounting hole 22, it is possible to mold first member 21 and second member 11 using the same basic metal die and by only changing an accessory metal die.

Moreover, since locking pieces 18 and 28 are provided on the right and left of optical connector plug 10 and locking pieces 18 and 28 are locked to engaged section 115 of receptacle case 114 when optical connector plug 10 is connected to optical connector receptacle 110, optical connector plug 10 is firmly connected to optical connector receptacle 110 and cable 80 of optical probe 1 is designed not to be easily disconnected even when cable 80 of optical probe 1 is pulled.

In optical connector plug 10, optical probe 1 and the optical system of the present embodiment, the number of parts of optical connector plug 10 is small, the parts can be easily assembled and the costs of optical connector plug 10 and optical probe 1 can thereby be reduced. Since three ferrules 30 are held by holding member 50 in a manner slightly displaceable, three ferrules 30 can be accurately connected to optical connector receptacle 110 even if a small error is generated in the molding size of the housing (first member 21 and second member 11). Therefore, it is possible to make the molding accuracy of the housing lower than the molding accuracy of resin parts of a general optical connector for optical communication, and thereby reduce the costs of optical connector plug 10 and optical probe 1.

More specifically, ferrule 30 can be easily held by holding member 50 by pushing the rotatably asymmetric flange portions (circular flange 32 and rectangular flange 33) of ferrule 30 into holding section 53 of holding member 50 from one side.

Since a conventional optical connector plug for optical communication is designed on the assumption that each component is accurately molded, a guide frame surrounding externally protruding ferrules is normally provided, but such a guide frame is eliminated in optical connector plug 10 of the present embodiment. This eliminates the necessity for aligning the guide frame on the plug side and on the receptacle side and makes it possible to lower the molding accuracy of the housing accordingly. Creating a complicated structure such as the guide frame through injection molding of resin may cause the yield to deteriorate, but since such a complicated structure is eliminated, it is possible to increase the yield and contribute to a cost reduction.

Since ferrule 30 is provided with lateral hole 37 and optical fiber 85 inserted into ferrule 30 is fixed by an adhesive or a fixing member such as a screw inserted into lateral hole 37, ferrule 30 and optical fiber 85 can be assembled more easily.

The present invention is not limited to the above embodiment, but various changes can be made. For example, the above embodiment has described a configuration in which a plurality of optical routes can be connected at a time, but the present invention may also be adopted for an optical connector provided with one ferrule and one receptacle part. Furthermore, in the above embodiment, the mounting hole of protrusion 70 for up/down orientation identification is provided only in first member 21, but such mounting holes may be provided in both first member 21 and second member 11 so that first member 21 and second member 11 become completely identical members. In this case, protrusion 70 may be attached to only one of first member 21 and second member 11 and the other mounting holes of first member 21 and second member 11 may be covered with a seal or the like. The above embodiment has described a configuration in which the cable conductor of the optical fiber is inserted through ferrule 30 via inner ferrule 41, but a coated optical fiber may be inserted up to the distal end of ferrule 30 and fixed. Furthermore, lateral hole 37 of ferrule 30 may be provided at a plurality of angle positions in the rotating direction about the optical axis. In addition, details shown in the embodiment such as the parts and shapes of the parts can be modified as appropriate without departing from the spirit and scope of the present invention.

The disclosure of Japanese Patent Application Nos. 2011-112606 and 2011-112608, filed on May 19, 2011, including the specification, drawings and abstract is incorporated herein by reference in their entirety.

INDUSTRIAL APPLICABILITY

The present invention is applicable to an optical probe used for a medical fluorescence detection apparatus, for example, and an optical connector plug and an optical system thereof.

REFERENCE SIGNS LIST

1 Optical probe
10 Optical connector plug
11 Second member
14 Engaging section
15 Engaging section
16 Engaged section
17 Semicircular groove
18 Locking piece
18a Locking lug
18b Protrusion
19a Semicanal groove
21 First member
24 Engaging section
25 Engaging section
26 Engaged section
27 Semicircular groove
28 Locking piece
28a Locking lug
28b Protrusion
29a Semicanal groove
30 Ferrule
32 Circular flange
33 Rectangular flange
37 Lateral hole
41 Inner ferrule
50 Holding member
51 Fixing section
51a Insertion hole
53 Holding section
53a, 53b Pinching piece
80 Cable
83 Binding hardware
85 Optical fiber
100 Optical apparatus
110 Optical connector receptacle
112 Receptacle part
114 Receptacle case
115 Locked portion

The invention claimed is:

1. An optical connector plug comprising:
an optical fiber;
a ferrule to which the optical fiber is connected;
a housing that covers the optical fiber and the ferrule, wherein the housing comprises:
a first member including at least an undersurface portion that covers an underside of an arrangement space in which the optical fiber and the ferrule are arranged, a half of a rear surface portion from which the optical fiber is led out, and a half of a front surface portion from which the ferrule is led out, the undersurface portion, the half of the rear surface portion and the half of the front surface portion being integrally molded of thermoplastic resin; and
a second member including at least a top surface portion that covers an upper side of the arrangement space, the remaining half of the rear surface portion and the remaining half of the front surface portion, the top surface portion, the remaining half of the rear surface portion and the remaining half of the front surface portion being integrally molded of thermoplastic resin into a shape identical to the shape of the first member; and
two locking pieces having a cantilever structure, the locking pieces being disposed on opposite sides of the housing and each having a locking lug at a distal end, wherein one of the two locking pieces in the entirety thereof is integrally formed on the first member, and wherein the other of the two locking pieces in the entirety thereof is integrally formed on the second member.

2. The optical connector plug according to claim 1,
wherein one or both of the first member and the second member are provided with an insertion hole to mount the member, and
wherein an orientation identification member that protrudes from an outer surface and can provide indication of orientation of the housing is attached to only one of the first member and the second member via the insertion hole.

3. An optical connector plug comprising:
an optical fiber;
a ferrule to which the optical fiber is connected; and
a housing that covers the optical fiber and the ferrule, wherein the housing comprises:
a first member including at least an undersurface portion that covers an underside of an arrangement space in which the optical fiber and the ferrule are arranged, a half of a rear surface portion from which the optical fiber is led out, and a half of a front surface portion from which the ferrule is led out, the undersurface portion, the half of the rear surface portion and the half of the front surface portion being integrally molded of thermoplastic resin; and a second member including at least a top surface portion that covers an upper side of the arrangement space, the remaining half of the rear surface portion and the remaining half of the front surface portion, the top surface portion, the remaining half of the rear surface portion and the remaining half of the front surface portion being integrally molded of thermoplastic resin into a shape identical to the shape of the first member, wherein the first member comprises an engaging section and an engaged section arranged at positions symmetric with respect to a plane that passes through each center of the front surface portion, the undersurface portion and the rear surface portion, wherein the second member comprises an engaging section to be engaged with the engaged section of the first member and an engaged section to be engaged with the engaging section of the first member at positions symmetric with respect to a plane that passes through each center of the front surface portion, the top surface portion and the rear surface portion, and wherein the first member and the second member are coupled together by engagements between the engaging section and the engaged section of the first member and between the engaged section and the engaging section of the second member.

4. The optical connector plug according to claim 3, wherein the engaging section of the first member comprises two piece members that stands upright side by side on the undersurface portion, the piece members each having a locking lug at each distal end, wherein the engaging section of the second member comprises two piece members that stands upright side by side on the top surface portion, the piece members each having a locking lug at each distal end, and wherein the two piece members are provided side by side in a direction from the rear surface portion toward the front surface portion.

5. The optical connector plug according to claim 3, wherein the first member and the second member comprise a semicanal cable holding groove that surrounds the optical fiber inside the rear surface portion from the top surface portion side and the undersurface portion side respectively, and wherein a lateral groove that extends in a direction orthogonal to an optical axis of the optical fiber is provided inside the cable holding groove.

6. An optical system comprising:

an optical probe including an optical connector plug comprising:
  an optical fiber;
  a ferrule to which the optical fiber is connected;
  a housing that covers the optical fiber and the ferrule, wherein the housing comprises:
    a first member including at least an undersurface portion that covers an underside of an arrangement space in which the optical fiber and the ferrule are arranged, a half of a rear surface portion from which the optical fiber is led out, and a half of a front surface portion from which the ferrule is led out, the undersurface portion, the half of the rear surface portion and the half of the front surface portion being integrally molded of thermoplastic resin; and
    a second member including at least a top surface portion that covers an upper side of the arrangement space, the remaining half of the rear surface portion and the remaining half of the front surface portion, the top surface portion, the remaining half of the rear surface portion and the remaining half of the front surface portion being integrally molded of thermoplastic resin into a shape identical to the shape of the first member; and
  two locking pieces having a cantilever structure, the locking pieces being disposed on opposite sides of the housing and each having a locking lug at a distal end, wherein one of the two locking pieces in the entirety thereof is integrally formed on the first member, and wherein the other of the two locking pieces in the entirety thereof is integrally formed on the second member; and an optical apparatus including an optical connector receptacle connected to the optical connector plug, wherein the optical connector receptacle comprises a locked portion with which the locking piece of the optical connector plug is locked when the optical connector plug and the optical connector receptacle are connected.

* * * * *